(12) United States Patent
Hermet et al.

(10) Patent No.: US 7,832,293 B2
(45) Date of Patent: Nov. 16, 2010

(54) METHOD AND DEVICE FOR DRAWING AND MIXING LIQUID SAMPLES

(75) Inventors: Jean-Pierre Hermet, Boulogne (FR);
Isabelle Besson-Faure, Aubagne (FR);
Sébastien Ribault, Plan de Cuques (FR);
Thomas Vigneron, Marseilles (FR)

(73) Assignee: Hemosystem, Marseilles (FR)

( * ) Notice: Subject to any disclaimer, the term of this patent is extended or adjusted under 35 U.S.C. 154(b) by 580 days.

(21) Appl. No.: 10/561,382

(22) PCT Filed: Jun. 17, 2004

(86) PCT No.: PCT/FR2004/001515

§ 371 (c)(1),
(2), (4) Date: Mar. 12, 2007

(87) PCT Pub. No.: WO2004/113878

PCT Pub. Date: Dec. 29, 2004

(65) Prior Publication Data

US 2007/0272039 A1     Nov. 29, 2007

(30) Foreign Application Priority Data

Jun. 17, 2003    (FR) .................................. 03 07305

(51) Int. Cl.
*G01N 1/00* (2006.01)
(52) U.S. Cl. .................................................. 73/864.81

(58) Field of Classification Search .............. 73/863.01, 73/864.81, 864.21, 864.83; 422/67, 68.1, 422/62, 63, 70; 436/43, 52
See application file for complete search history.

(56) References Cited

U.S. PATENT DOCUMENTS

| | | | | | |
|---|---|---|---|---|---|
| 3,856,634 | A | * | 12/1974 | Hahn et al. | 205/782 |
| 4,333,356 | A | * | 6/1982 | Bartels et al. | 73/864.21 |
| 4,794,806 | A | * | 1/1989 | Nicoli et al. | 73/863.01 |
| 5,259,812 | A | * | 11/1993 | Kleinsek | 454/57 |
| 5,403,304 | A | * | 4/1995 | Ishida | 604/403 |
| 5,627,346 | A | * | 5/1997 | Weibel et al. | 177/64 |
| 2001/0013579 | A1 | * | 8/2001 | Andrien et al. | 250/423 R |
| 2003/0013199 | A1 | * | 1/2003 | Anderson et al. | 436/50 |

FOREIGN PATENT DOCUMENTS

| AU | 9470269 A * | 3/1995 |
|---|---|---|
| FR | 2784023 A1 * | 4/2000 |

* cited by examiner

*Primary Examiner*—Hezron Williams
*Assistant Examiner*—Tamiko D Bellamy
(74) *Attorney, Agent, or Firm*—Bachman & LaPointe, P.C.

(57) ABSTRACT

A method and device for continuously drawing and mixing liquid samples originating from at least two different containers are described. The device comprises a mixing chamber, which is connected to each of the containers. The device is characterized in that it comprises, between the container and the mixing chamber, at least one intermediate sample chamber for each container, being connected in order to transfer all or a portion of the sampled liquid to the mixing chamber. The device has a vertical configuration.

23 Claims, 3 Drawing Sheets

METHOD AND DEVICE FOR DRAWING AND MIXING LIQUID SAMPLES

BACKGROUND OF THE INVENTION (1) Field of the Invention

The present invention relates to the field of preparation of liquid samples with a view to their analysis.

The present invention relates more particularly to a method and a device for drawing and mixing liquid samples originating from at least n (n≧2) different containers.

(2) Prior Art

Such methods and/or devices for drawing and mixing liquid product samples are already known in the prior art.

In the United States document US H1960 H, a method and a device are proposed which are intended to analyse donations of blood or plasma with a view to detecting the specific donations having contamination by a virus, greater than a pre-established level. The method comprises a first step consisting of forming containers of unitary samples, sealed separately and interconnected, using a flexible hollow tubing segment connected to a container of donations of fluid. It is therefore a matter of drawing n times a given volume of a sample originating from a container. This step is repeated for n containers of donations of biological liquids. Advantageously, each container of samples is formed in order to contain approximately 0.02 to 0.5 ml of blood or plasma. A second step then consists of transferring identical volumes of a sample obtained in step 1 into a mixing container. At this step, a sample from the n containers obtained is drawn.

Thus, according to one example embodiment of the invention described in US H1960 H, the drawing and mixing device comprises a central hollow tubular collection container connected to a vacuum source, and under which needles are connected for automatic drawing of blood or plasma from the unitary containers. Thus, once the needles are disposed to pierce through the unitary containers containing the blood or plasma samples, the vacuum is applied to the container so that the blood or plasma samples rise up through the needles into the container. Advantageously, in order to prevent any contamination, the drawing devices (needles for example) are sterilised or replaced so that cleaned or sterile devices are used between each mixture formed.

Also proposed in the U.S. Pat. No. 5,364,526 is a system making it possible to conduct, into a receiving or transfer container, biological fluid disposed in independent containers (at least two independent containers). This transfer takes place via a grouping device consisting of a plurality of pieces of tubing, said grouping device being in communication respectively with each of the independent containers and the receiving container. Advantageously, the elements constituting the system are disposed in a vertical arrangement, the independent containers being disposed above the receiving container. Once full, the receiving container is hermetically sealed and separated from the system, without air being introduced into said container. Advantageously, the system is a sterile system.

However, the method and system described in the aforementioned documents have drawbacks.

In particular, the method described by US H1960 H discloses a discontinuous method. It emerges in fact that, prior to the drawing of the samples, it is necessary to place pre-formed samples in an apparatus in order to allow the drawing of each of the pre-formed samples. The result is therefore a tedious and long method.

As regards the system described in U.S. Pat. No. 5,364,526, this, through its construction, offers no guarantee of drawing sterility. This is because the piece of tubing originating from each independent container is in contact with at least one other piece of tubing originating from another independent container. Such a system therefore does not allow drawings from containers to be isolated from one another.

SUMMARY OF THE INVENTION

The present invention intends to remedy the drawbacks of the prior art by proposing a method and a device allowing the continuous drawing and mixing of liquids originating from different original containers whilst avoiding the contamination of said original containers.

To do this, the object of the present invention is to propose a method for continuously drawing and mixing liquid samples originating from at least n (n≧2) different containers, characterised in that it comprises successively the steps consisting of:

drawing a given volume of n samples originating from n different containers of liquids, each of the samples drawn being placed in a sampling chamber;

transferring identical volumes of each sample drawn at the preceding step into a common mixing container in order to obtain a mixture sample to be analysed.

Advantageously, the drawing step consists of drawing a volume of liquid from each container comprising between 0.5 and 20 milliliters, and preferentially between 2 and 8 milliliters.

Advantageously, the step of transferring to the mixing container consists of transferring a volume of each drawn sample comprising between 0.5 and 20 milliliters, and preferentially between 2 and 8 milliliters.

Advantageously, the step of transferring the drawn samples into the mixing container is initiated by an external action.

Advantageously, the step of transferring the drawn samples into the mixing container is initiated automatically.

Advantageously, the drawing of the liquid samples of the first step is performed in a sterile manner.

Another aim of the present invention is to propose a continuous method for the analysis of biological liquids, characterised in that it comprises successively the steps consisting of:

drawing a given volume of n samples originating from n (n≧2) different containers of liquids, each of the samples drawn being placed in a sampling chamber;

transferring identical volumes of each sample drawn at the preceding step into a common mixing container in order to obtain a mixture sample to be analysed;

transferring a given volume of the mixture sample to be analysed from the preceding step to an analysis device.

Advantageously, the step of transferring to the analysis device consists of transferring a minimum volume of 1 milliliter of the mixture sample.

Advantageously, the transfer at least in part of the mixture sample to the analysis device is performed aseptically.

The present invention also relates to a device for drawing and mixing samples of liquids originating from at least two different containers, said device comprising a mixing chamber connected to each of said containers, characterised in that said device comprises, between the container and the mixing chamber, at least one intermediate sampling chamber for each container, connected so as to transfer to said mixing chamber all or part of the sampled liquid, and in that said device is configured in a vertical arrangement.

Preferably, said mixing chamber is disposed under said sampling chambers.

Advantageously, the mixing chamber is associated in a removable manner with the sampling chambers.

Advantageously, the connection between the containers and the sampling chambers consists of a piece of tubing, a tap, a stopper that can be pierced by a needle or a screw-fitting sealed by a stopper.

Advantageously, the connection between the sampling chambers and the mixing chamber consists of a tube, a breakable fitting, a tap or a tubing clip.

Advantageously, the mixing chamber is sealed by means of a screwed stopper, a stopper that can be pierced by a needle, a tap or a piece of tubing.

Advantageously, said device comprises at least one non-return valve.

Advantageously, the drawing and mixing device is a sterile device.

Advantageously, the drawing and mixing device is a device that can be sterilised, preferably by β or γ irradiation.

Advantageously, said device comprises connection means for connecting said drawing and mixing device to an analysis device.

Advantageously, the connection between the drawing and mixing device and the analysis device is an aseptic connection.

Advantageously, the sampling chambers and/or the mixing chamber consist(s) of a flexible plastic material, of the PVC type.

BRIEF DESCRIPTION OF THE DRAWINGS

The invention will be better understood with the help of the description, given below purely by way of explanation, of one embodiment of the invention, with reference to the accompanying figures.

DETAILED DESCRIPTION OF THE PREFERRED EMBODIMENT(S)

The invention concerns a method and a device for drawing and mixing samples of liquid products originating from different containers.

In the following examples, the samples of liquid products relate to samples of unstable blood products originating from bags. The objective of the device, in the examples described, is the continuous sterile preparation of samples of given volume, for the rapid detection of rare occurrences in said samples, such as the detection of bacteria or contaminating agents.

It is of course obvious that the application to unstable blood products is given here by way of an example and that the invention is in no way limited to this.

It is of course also obvious that the objective related to the detection of rare occurrences is also given by way of an example, in no way limiting the invention.

Figure 1:
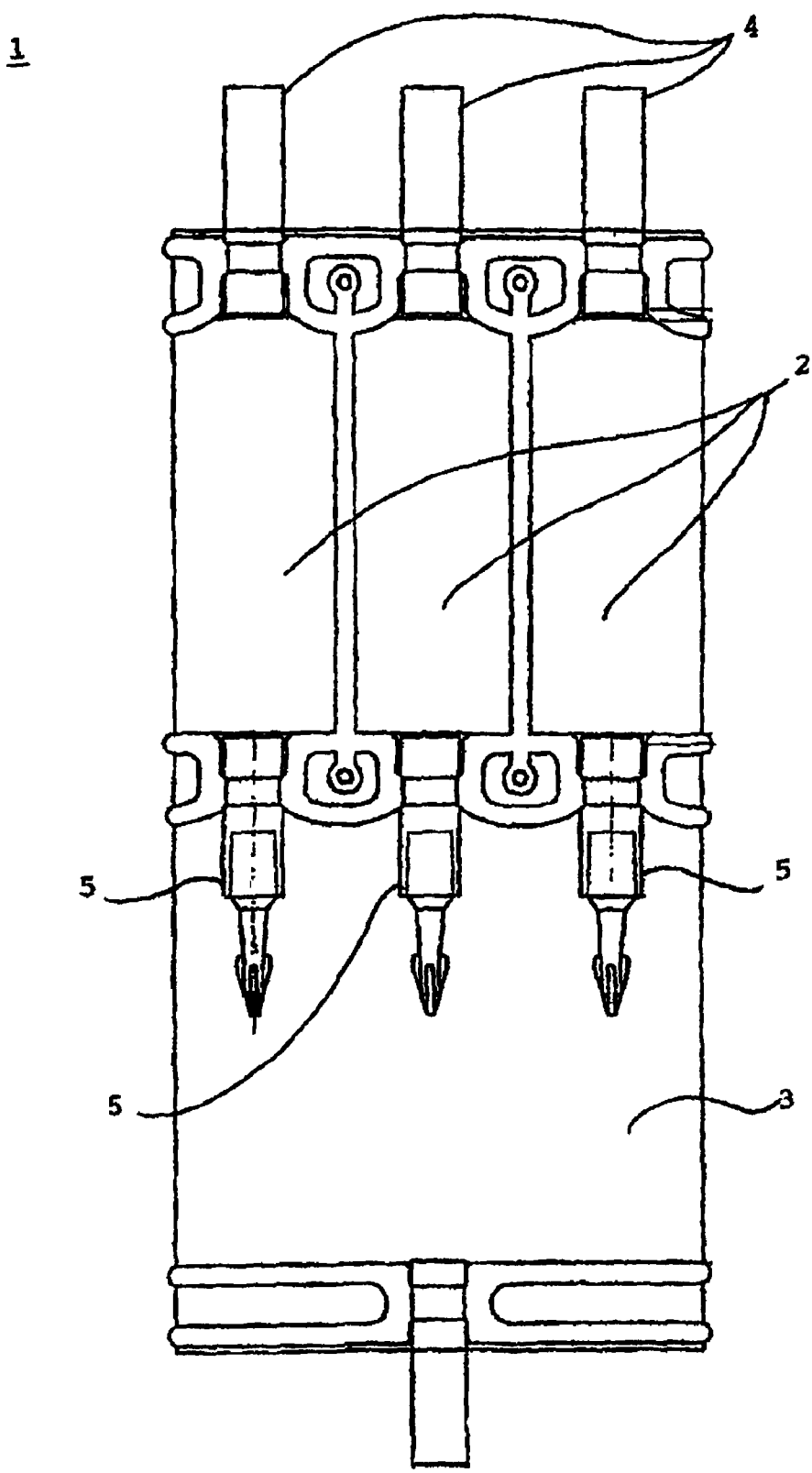
FIG. 1 illustrates a sectional view of a device for drawing and mixing samples of biological liquids according to a first embodiment of the invention.

FIG. 1 illustrates a first embodiment of said drawing and mixing device (1) of the invention.

Said device (1) consists, in this example embodiment, of three sampling chambers (2) aligned in a horizontal plane. A mixing chamber (3) is disposed under said sampling chambers.

Each of said sampling chambers (2) is connected via pieces of tubing (4) disposed on its upper part to separate bags of unstable blood products originating from different donors (not depicted), which are also equipped with pieces of tubing.

The connection between the drawing chambers (2) and the bags of blood will be implemented so as to allow sterile drawing.

Means, other than the pieces of tubing, may also be suitable for implementing the connection between the sampling chambers (2) and the bags of blood. They may be taps, plugs able to be pierced by a needle, or else a screw-fitting sealed by a stopper.

Each sampling chamber (2) is also equipped with a conveying tube (5), each of the tubes being intended to transfer, to said mixing chamber (3), all or part of the blood samples drawn from said bags of blood and contained in said sampling chambers (2).

Figure 3:
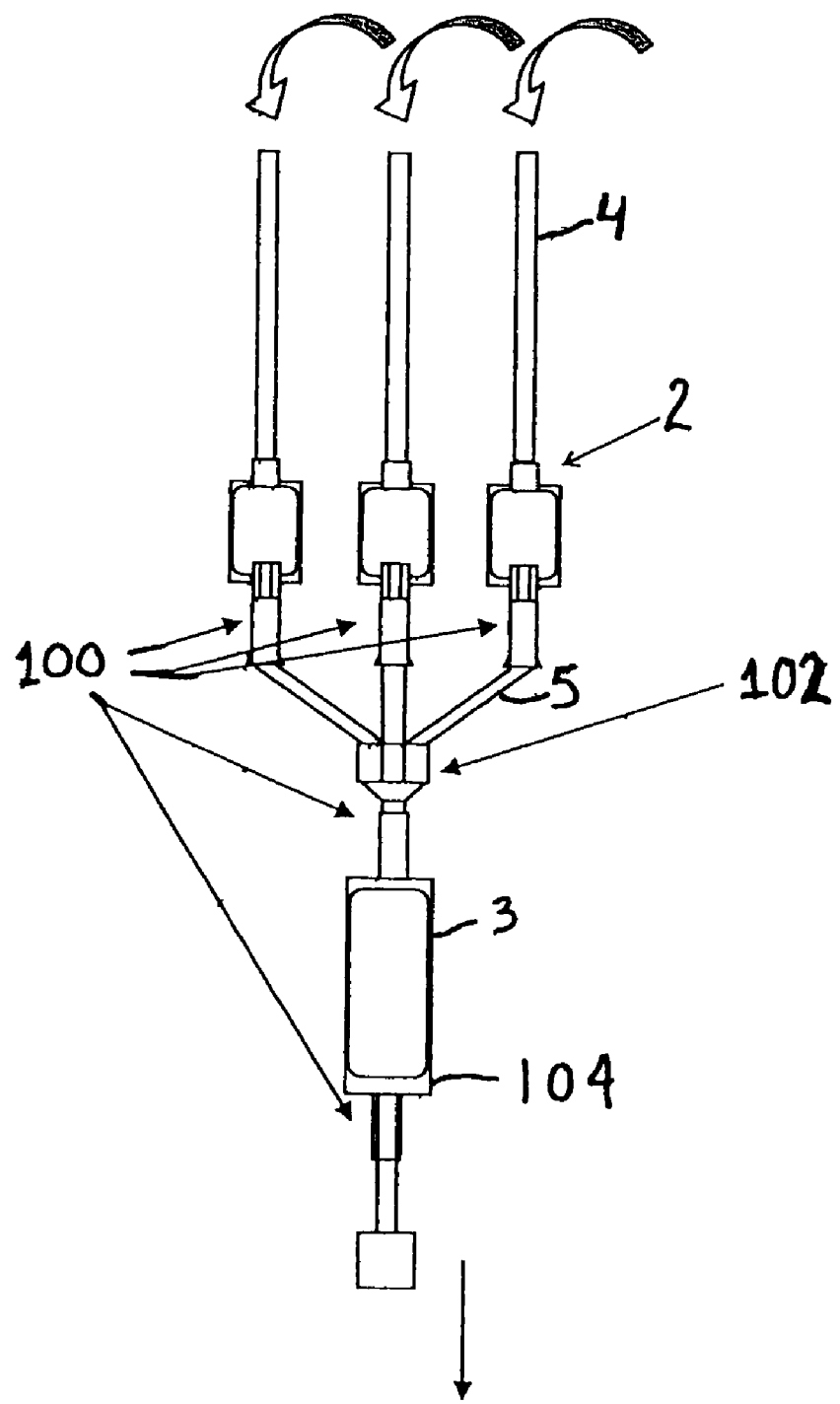
FIG. 3 illustrates a sectional view of a device for drawing and mixing samples of biological liquids.

Advantageously, the conveying tubes (5) consist of a breakable fitting (100) to allow the blood sample contained in a sampling chamber (2) to flow to the mixing chamber (3). As can be seen from FIG. 3, the connection between the sampling chambers (2) and the mixing chamber (3) can consist of a tube (5), a breakable fitting (100), and an element (102) which is a tap or a tubing clip. Further, the mixing chamber (3) can be sealed by means of an element (104) such as a screwed stopper, a stopper that can be pierced by a needle, a tap or a piece of tubing.

The device according to the invention has the advantage of making it possible to eliminate any risk of contamination of said samples.

This is because the part of said device (1) intended for the drawing of said samples can advantageously be sterilised by β or γ irradiation, so that the risks of contamination of the samples by micro-organisms are eliminated.

Moreover, the envisaged connections make it possible to reduce as much as possible the risks of contamination of the samples by micro-organisms; the use in particular of tubing-to-tubing connection facilitates sterile connection. It concerns the case where the blood samples are drawn from bags of blood. It is then essential for the tubing to have an internal diameter of 3 millimeters and an external diameter of 4 millimeters.

In addition, the samples are drawn so that each sample cannot under any circumstances be contaminated by the samples from the other bags, so as to avoid sample-to-sample reactions for the parameters to be quantitatively analysed which are sensitive to their environment. In this case, the mixing will be performed at the time of the analysis to be performed on the mixed samples in order to reduce sample-to-sample contacts as much as possible.

Said device (1) also comprises connection means in order to be connected to an analysis device (not depicted) intended to detect in the mixture sample the presence of rare occurrences such as bacteria.

Advantageously, the connection is an aseptic connection.

In the example illustrated in FIG. 1, the connection between the drawing and mixing device and the analysis device is implemented by means of tubing. It can also be implemented by means of a breakable fitting. In this case, prior to the connection of the mixing chamber to the analysis device, said mixing chamber is sealed by means of a stopper screwed onto said fitting.

Other means allowing the sealing of the mixing chamber but also the connection of said mixing chamber to said analysis device can of course be envisaged. In particular, such means can consist of a stopper that can be pierced by a needle or a tap.

Advantageously, the drawing and mixing device (1) is made from a material able to withstand γ or β irradiation and welding actions. Advantageously, said sampling chambers and/or the mixing chamber (1) consist(s) of a flexible material, preferably made of PVC.

Advantageously, the sampling chambers are formed from a single bag which is shaped by welding to have the desired number of sampling chambers (in this case in this example embodiment, three sampling chambers).

The method for drawing and mixing samples used with the device (1) of FIG. 1 is presented below.

The first step consists of drawing in a sterile manner a given volume of three samples originating from three bags of blood originating from different donors. As explained previously, the drawing is performed so as to avoid the possibility of each bag drawn from being contaminated by the samples drawn from the other two bags. To do this, the drawing is advantageously implemented by means of a tubing-to-tubing connection. Each of said drawn samples is then respectively placed in the sampling chambers (2) which are independent of one another.

The drawing step consists of drawing from each of the bags preferentially a volume comprising between 2 milliliters and 8 milliliters. Furthermore, each bag of blood can be drawn from simultaneously or successively.

The following step consists of transferring an identical volume comprising preferentially between 2 milliliters and 8 milliliters of each drawn sample into said mixing chamber (3) in order to obtain the mixture sample to be analysed. This step of transferring all or part of the blood sample contained in the sampling chambers (2) to the mixing chamber (3) is initiated manually by a user. In fact the user carries out, through said mixing chamber consisting of a flexible material of the PVC type, an action to break the breakable fittings linking the sampling chambers (2) to the mixing chamber.

Once the fittings have been broken, the samples contained in the sampling chambers (2), which are disposed in a vertical arrangement, flow by gravity into the mixing chamber (3). Advantageously a pressure can be exerted on the sampling chambers (2) to accelerate the mixing.

The mixture sample thus obtained is transferred to said analysis device to be analysed, this analysis making it possible to determine whether or not said mixture sample comprises bacteria. The volume of mixture sample transferred to said detection device will be a minimum of 1 milliliter.

Advantageously, the transfer of the mixture sample to the analysis device is performed aseptically.

As seen in the example described previously, the drawing and mixing device (1) is constituted so that the mixing chamber (3) is associated with or can be directly fixed on the sampling chambers (2). It is of course obvious that said mixing chamber (3) can constitute an element separate from the sampling area formed by said sampling chambers (2) as illustrated in FIG. 2.

Figure 2:
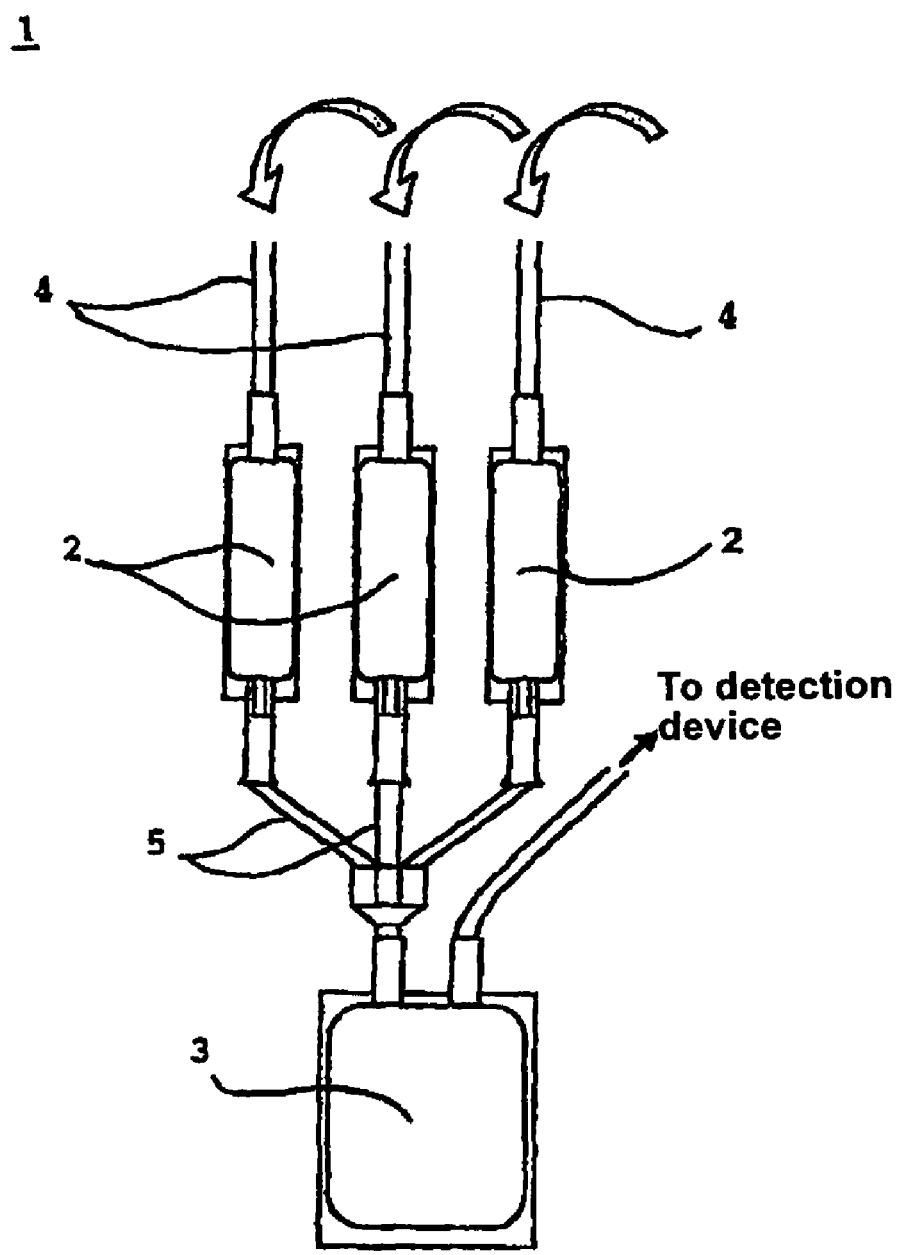
FIG. 2 illustrates a sectional view of a device for drawing and mixing samples of biological liquids according to a second embodiment of the invention.

The examples illustrated in FIGS. 1 and 2 describe the drawing of three blood samples. It is of course obvious that the device (1) according to the invention is configured to draw and mix n samples, n being an integer number greater than or equal to two.

According to a variant implementation of the invention, a reaction medium can be placed in the mixing chamber, within the context of preparing for the analysis of the mixture sample in the detection device to which said sample is going to be transferred.

Similarly, depending on the analysis provided for, a reaction medium can also be placed in each of the sampling chambers. This can be for example a medium allowing the growth of bacteria.

Moreover, the embodiments presented by way of example refer to samples of identical liquids. It should be understood that the samples originating from different bags can relate to different liquids.

The invention is described above by way of an example. It should be understood that persons skilled in the art are able to implement different variants of the invention without for all that departing from the scope of the patent.

The invention claimed is:

1. A method for continuously drawing and mixing liquid samples originating from at least n different containers where n is greater than or equal to 2, said method comprising the steps of:
   drawing a given volume of n samples originating from n different containers of liquids;
   placing each of the samples drawn respectively in at least one of n different intermediate sampling chambers; and
   transferring by gravity identical volumes of each sample drawn into a sealed common mixing container for obtaining, after mixing of volumes transferred into the sealed common mixing container, a mixture sample to be analyzed.

2. A method for continuously drawing and mixing liquid samples according to claim 1, wherein the drawing step consists of drawing a volume of liquid from each container comprising between 0.5 and 20 milliliters.

3. A method for continuously drawing and mixing liquid samples according to claim 1, wherein the drawing step consists of drawing a volume of liquid from each container comprising between 2 and 8 milliliters.

4. A method for continuously drawing and mixing liquid samples according to claim 1, wherein the step of transferring to the mixing container consists of transferring a volume of each drawn sample comprising between 0.5 and 20 milliliters.

5. A method for continuously drawing and mixing liquid samples according to claim 1, wherein the step of transferring to the mixing container consists of transferring a volume of each drawn sample comprising between 2 and 8 milliliters.

6. A method for continuously drawing and mixing liquid samples according to claim 1, wherein the step of transferring the drawn samples into the mixing container is initiated by an external action.

7. A method for continuously drawing and mixing liquid samples according to claim 1, wherein the step of transferring the drawn samples into the mixing container is initiated automatically.

8. A method for continuously drawing and mixing liquid samples according to claim 1, wherein the drawing of the liquid samples of the first step is performed in a sterile manner.

9. A continuous method for the analysis of liquids, said method comprising the steps of:
   drawing a given volume of n samples originating from n different containers of liquids where n is greater than or equal to 2;
   placing each of the samples drawn respectively in at least one of n different intermediate sampling chambers;

transferring by gravity identical volumes of each sample drawn into a sealed common mixing container and obtaining a mixture sample to be analyzed; and transferring a given volume of the mixture sample to be analyzed to an analysis device.

10. A continuous method for the analysis of liquids according to claim 9, wherein the step of transferring to the analysis device consists of transferring a minimum volume of 1 milliliter of the mixture sample.

11. A continuous method for the analysis of liquids according to claim 9, wherein said transferring step comprises transferring at least part of the mixture sample to the analysis device aseptically.

12. A device for drawing and mixing samples of liquids originating from at least two different containers, said device comprising a sealed mixing chamber connected to each of said containers, at least one intermediate sampling chamber between each said container and the sealed mixing chamber, said at least one intermediate sampling chamber being connected so as to transfer to said sealed mixing chamber at least part of the sampled liquid, said device being configured in a vertical arrangement, and the sealed mixing chamber being disposed under said at least one intermediate sampling chamber and connected to said at least one intermediate sampling chamber so that the samples of liquid contained in the at least one intermediate sampling chamber flow by gravity into the sealed mixing chamber.

13. A device for drawing and mixing liquid samples according to claim 12, wherein the mixing chamber is associated in a removable manner with the intermediate sampling chambers.

14. A device for drawing and mixing liquid samples according to claim 12, wherein a connection between the containers and the intermediate sampling chambers comprises a piece of tubing, a tap, and a stopper that can be pierced by a needle or a screw-fitting sealed by a stopper.

15. A device for drawing and mixing liquid samples according to any claim 12, wherein a connection between the intermediate sampling chambers and the mixing chamber comprises a tube, a breakable fitting, and a tap or a tubing clip.

16. A device for drawing and mixing liquid samples according to claim 12, wherein the mixing chamber is sealed by means of at least one of a screwed stopper, a stopper that can be pierced by a needle, a tap and a piece of tubing.

17. A device for drawing and mixing liquid samples according to claim 12, further comprising at least one non-return valve.

18. A device for drawing and mixing liquid samples according to claim 12, wherein the drawing and mixing device (1) is a sterile device.

19. A device for drawing and mixing liquid samples according to claim 12, wherein the drawing and mixing device is a device that can be sterilised by $\beta$ or $\gamma$ irradiation.

20. A device for drawing and mixing liquid samples according to claim 12, further comprising means for connecting said drawing and mixing device to an analysis device.

21. A device for drawing and mixing liquid samples according to claim 20, wherein the connecting means between the drawing and mixing device and the analysis device comprises an aseptic connection.

22. A device for drawing and mixing liquid samples according to claim 12, wherein at least one of the sampling chambers and the mixing chamber consists of a flexible PVC plastic material.

23. An assembly consisting of a device for drawing and mixing liquid samples according to claim 12 and an analysis device, said analysis device being connected to the mixing chamber of the device for drawing and mixing liquid samples so that the samples contained by the mixing chamber are transferred to the analysis device.

* * * * *